United States Patent [19]

Strickler et al.

[11] Patent Number: 5,556,997
[45] Date of Patent: Sep. 17, 1996

[54] ENHANCED SYNTHESIS OF RACEMIC METALLOCENES

[75] Inventors: Jamie R. Strickler; John M. Power, both of Baton Rouge, La.

[73] Assignee: Albemarle Corporation, Richmond, Va.

[21] Appl. No.: 427,505

[22] Filed: Apr. 24, 1995

[51] Int. Cl.$^6$ .............................. C07F 17/00; C07F 7/00; C07F 9/00
[52] U.S. Cl. ................... 556/11; 556/1; 556/12; 556/43; 556/47; 556/53; 534/11; 534/15; 526/943
[58] Field of Search .................... 556/1, 11, 12, 556/43, 47, 53; 534/11, 15; 526/943

[56] References Cited

U.S. PATENT DOCUMENTS

| | | | |
|---|---|---|---|
| 5,200,537 | 4/1993 | Lee et al. | 556/11 |
| 5,268,495 | 12/1993 | Rielp et al. | 556/11 |
| 5,302,733 | 4/1994 | Diefenbach et al. | 556/11 |
| 5,329,031 | 7/1994 | Miyake et al. | 556/12 |
| 5,329,033 | 7/1994 | Spaleck et al. | 556/53 |
| 5,336,795 | 8/1994 | Lisowsky | 556/56 |
| 5,391,789 | 2/1995 | Rohrmann | 556/11 |

FOREIGN PATENT DOCUMENTS

| | | |
|---|---|---|
| 2055218 | 5/1992 | Canada. |
| 0530908 | 3/1993 | European Pat. Off.. |
| 0581754 | 2/1994 | European Pat. Off.. |

OTHER PUBLICATIONS

Ray, T. C., et al., Inorg. Chem., 1965, 1501–1504.
Spaleck, Walter, et al., Angew. Chem. Int. Ed., 1992, 31, 1347–1350.
Spaleck, Walter, et al., Organometallics, 1994, 13, 954–963.

*Primary Examiner*—Porfirio Nazario-Gonzales
*Attorney, Agent, or Firm*—Philip M. Pippenger

[57] ABSTRACT

Chiral metallocenes are prepared by reacting a salt of an asymmetric bis(cyclopentadienyl) moiety containing ligand with a chelate diamine adduct of a transition, lanthanide, or actinide metal halide in an organic solvent medium so as to produce said chiral metallocene.

14 Claims, No Drawings

ENHANCED SYNTHESIS OF RACEMIC METALLOCENES

The invention relates generally to the preparation of metallocenes which are useful as stereoregular olefin polymerization catalysts and more specifically to a process for metallizing cyclopentadienyl ligand salts with certain transition, lanthanide or actinide metal compounds which are chelate diamine adducts of the metal halides.

As known in the art, metallocenes can be prepared by reacting a metal compound of the formula $MX_n$, where M is the metal, n is an integer of 1 to 6, depending upon the valence of M, and X is independently an anionic ligand group or a neutral Lewis base ligand group having up to 30 non-hydrogen atoms such as hydride, halo, alkyl, aryl, silyl, germyl, aryloxy, alkoxy, amide, and siloxy, with an alkali metal or a magnesium halide salt of a cyclopentadienyl ligand in a solvent such as an ether.

Chiral metallocenes are useful for the synthesis of polyolefins. Specifically, the racemic form of the metallocene provides stereoregular poly(alpha-olefins) in addition to being considerably more active than the meso form, which produces only atactic polymers. An efficient synthesis of chiral metallocenes that favors the formation of the racemic isomer at the metallation stage is desired. We have now found that by using certain chelate diamine adducts of a metal halide in the reaction with the salt of the cyclopentadienyl ligand, enhanced formation of the racemic isomer and/or better product yields can be produced, especially by using a mixed ether-hydrocarbon reaction solvent medium.

In accordance with this invention there is provided a process for preparing a chiral metallocene, said process comprising reacting a salt of an asymmetric bis(cyclopentadienyl) moiety containing ligand with a chelate diamine adduct of a transition, lanthanide or actinide metal halide in an organic solvent medium so as to produce said chiral metallocene.

Chiral metallocenes which can be prepared in accordance with the process of the invention preferably contain a metal from Groups 3–10, or the lanthanide and actinide series of the Periodic Table of the elements and, more preferably a Group 4 to 6 transition metal, which is coordinated with a ligand containing a pair of cyclopentadienyl moieties, at least one of which is asymmetric, which moieties are stereorigid such as by being joined by a bridging group. The cyclopentadienyl moieties can be substituted with one or more groups, such as halogen, amino, mercapto, phosphino, and $C_1$ to $C_{20}$ hydrocarbyl, silahydrocarbyl, or halohydrocarbyl and the like and can include moieties which are condensed, multi-ring structures such as, for example, indenyl, benzoindenyl, or fluorenyl, which structures can be hydrogenated and/or further substituted. The other groups on the metal atom usually include hydride, halogen, hydrocarbyl or halohydrocarbyl having up to about 6 carbons. Such chiral metallocenes, and their use as catalysts in forming isotactic olefin polymers are described, for example, in U.S. Pat. Nos. 5,017,714; 5,036,034; 5,145,819; 5,296,434; 5,324,800 and 5,329,033, whose disclosures are incorporated herein by reference. Typical bridging groups include silicon containing bridges of 1–4 atoms selected from silanylene, silaalkylene, oxasilanylene and oxasilaalkylene, such as, dimethylsilanylene. The chiral metallocenes are mixtures of racemic diasteriomers which have no plane of symmetry. In contrast, the meso isomers have a plane of symmetry running through the metal between the rings and are, therefore achiral.

Specific, non-limiting examples of chiral metallocenes include racemic:

[1,1'-dimethylsilanylene-bis(3-methylcyclopentadienyl)] zirconium dichloride;
[1,1'-dimethylsilanylene-bis(indenyl)]zirconium dichloride;
[1,1'-dimethylsilanylene-bis(4,5,6,7-tetrahydroindenyl)]zirconium dichloride;
[1,1'-(1,1,2,2-tetramethyldisilanylene)-bis(3-methylcyclopentadienyl)]zirconium dichloride;
[1,1'-(1,1,2,2-tetramethyldisilanylene)-bis(4,5,6,7-tetrahydroindenyl)]zirconium dichloride;
[1,1'-(dimethylsilanylene-bis( 3-trimethylsilanylcyclopentadienyl)]zirconium dichloride;
[1,1'-(1,1,2,2-tetramethyldisilanylene-bis(3-trimethylsilanylcyclopentadienyl)]zirconium dichloride;
[1,1'-(1,1,3,3-tetramethyldisilanylene-bis(4,5,6,7-tetrahydroindenyl)]zirconium dichloride;
[1,1'-(1,1,4,4-tetramethyl-1,4-disilanylbutylene-bis(4,5,6,7tetrahydroindenyl)]zirconium dichloride;
[1,1'-(2,2-dimethyl-2-silapropylene)-bis(3-methylcyclopentadienyl)]zirconium dichloride;
[1,1'-(dimethylsilanylene-bis(3-methylcyclopentadienyl)]titanium dichloride;
[1,1'-(dimethylsilanylene-bis(indenyl)]titanium dichloride;
[1,1'-dimethylsilanylene-bis(4,5,6,7-tetrahydroindenyl)]titanium dichloride;
[1,1'-(1,1,2,2-tetramethyldisilanylene)-bis(3-methylcyclopentadienyl)]titanium dichloride;
[1,1'-(1,1,2,2-tetramethyldisilanylene)-bis(4,5,6,7-tetrahydroindenyl)]titanium dichloride;
[1,1'-(dimethylsilanylene-bis( 3-trimethylsilanylcyclopentadienyl)]titanium dichloride;
[1,1'-(1,1,2,2-tetramethyldisilanylene)-bis(3-trimethylsilanylcyclopentadienyl)]titanium dichloride;
[1,1'-(1,1,3,3-tetramethyldisilanylene)-bis(4,5,6,7-tetrahydroindenyl)]titanium dichloride;
[1,1'-(1,1,4,4-tetramethyl- 1,4-disilanylbutylene)bis(4,5,6,7-tetrahydroindenyl)]titanium dichloride;
[1,1'-(2,2-dimethyl-2-silapropylene)-bis(3-methylcyclopentadienyl)]titanium dichloride;
[1,1'-dimethylsilanylene-bis(3-methylcyclopentadienyl)] hafnium dichloride;
[1,1'-dimethylsilanylene-bis(indenyl)]hafnium dichloride;
[1,1'-dimethylsilanylene-bis(4,5,6,7-tetrahydroindenyl)] hafnium dichloride;
[1,1'-(1,1,2,2-tetramethyldisilanylene)-bis(3-methylcyclopentadienyl)]hafnium dichloride;
[1,1'-(1,1,2,2-tetramethyldisilanylene)-bis(4,5,6,7-tetrahydroindenyl)]hafnium dichloride;
[1,1'-(dimethylsilanylene-bis( 3-trimethylsilanylcyclopentadienyl)]hafnium dichloride;
[1,1'-(1,1,2,2-tetramethyldisilanylene-bis(3-trimethylsilanylcyclopentadienyl)]hafnium dichloride;
[1,1'-(1,1,3,3-tetramethyldisilanylene-bis(4,5,6,7-tetrahydroindenyl)]hafnium dichloride;
[1,1'-(1,1,4,4-tetramethyl-1,4-disilanylbutylene-bis( 4,5,6,7-tetrahydroindenyl)]hafnium dichloride;
[1,1'-(2,2-dimethyl-2-silapropylene)-bis(3-methylcyclopentadienyl)]hafnium dichloride;
dimethylsilylbis(1-(2-methyl-4-ethylindenyl)zirconium dichloride;
dimethylsilylbis(1-(2-methyl-4-isopropylindenyl))zirconium dichloride;
dimethylsilylbis(1-(2-methyl-4-tert-butylindenyl))zirconium dichloride;
methylphenylsilylbis(1-(2-methyl-4-isopropylindenyl))zirconium dichloride;
dimethylsilylbis(1-(2-ethyl-4-methylindenyl)zirconium dichloride;

dimethylsilylbis(1-(2,4-dimethylindenyl))zirconium dichloride;
dimethylsilylbis(1-(2-methyl-4-ethylindenyl))zirconium dimethyl;
dimethylsilyl(2-methyl-4,5,6,7-tetrahydro-1-indenyl)$_2$zirconium dichloride;
ethylene(2-methyl-4,5,6,7-tetrahydro-1-indenyl)$_2$zirconium dichloride;
dimethylsilyl(2-methyl-4,5,6,7-tetrahydro-1-indenyl)$_2$dimethyl zirconium;
phenyl(methyl)silyl(indenyl)$_2$zirconium dichloride;
dimethylsilyl (2,3,5-trimethyl-1-cyclopentadienyl)$_2$zirconium dichloride;
dimethylgermyl(indenyl)$_2$zirconium dichloride;
ethylene(indenyl)$_2$zirconium dichloride;
methylene(3-t-butyl-1-cyclopentadienyl)$_2$zirconium dichloride;
dimethylsilyl(4,7-dimethyl-1-indenyl)$_2$zirconium dichloride;
dimethylsilanyl-bis(indenyl)thorium dichloride; and
dimethylsilanyl-bis(indenyl)uranium dichloride.

The metallocenes are prepared by first deprotonating the appropriate ligand compound using an alkali metal, an alkali metal salt, or a Grignard reagent to form an alkali metal or magnesium halide salt of the ligand. Examples of deprotonizing agents include Na powder, RLi, NaH, LiH and RMgX, where R is $C_1$ to $C_{10}$ hydrocarbyl and X is halogen. Preferred are alkyllithium compounds such as methyllithium, n-butyllithium, s-butyllithium, t-butyllithium, phenyllithium, and the like.

Suitable reaction solvents are aliphatic or aromatic hydrocarbon or halocarbon solvents and acyclic or cyclic ethers. Mixed ether and hydrocarbon or halohydrocarbon solvents in ratios of from about 9:1 to 1:9 by volume ether to hydrocarbon solvent and, preferably, 4:1 to 1:2 provide improved yields of the metallocenes having increased racemic isomer content. Examples of suitable solvents include diethyl ether, tetrahydrofuran (THF), ethylene glycol dimethyl ether, hexanes, cyclohexane, heptane, pentane, toluene, benzene, xylene, chlorobenzene and the like. Mixtures of THF and toluene are preferred to provide enhanced yields of racemic isomer enriched product.

The ligand salt, such as the dilithium salt, from the deprotonation is reacted with a chelate diamine adduct of a transition, lanthanide or actinide metal compound and, preferably a metal halide, in order to form the racemic metallocene. Suitable diamines for forming the adducts which are effective to provide metallocenes with an enhanced yield of racemic isomer, include tetramethylene tertiary diamines and especially N,N,N'N'-tetramethylethylenediamine (TMEDA) and tetramethyldiaminomethane (TMDAM). A metal chloride to diamine ratio of 1:0.5 to 1:5 provides improved yields of the racemic metallocene. About equimolar to about a 10% excess of diamine is preferably used. Preferably, the diamine adduct of the metal is formed prior to mixing it with the ligand.

Non-limiting examples of transition, lanthanide and actinide metals include Ti, Zr, Hf, V, Cr, La, Ce, Th, U, and the like. Preferred for catalyst use are the Group 4 metals Ti, Zr and Hf.

The adducts can be prepared in hydrocarbon solvents such as those named above for the deprotonation reaction and, preferably toluene, and either separated from the solvent, such as by filtration, or the adduct in solvent can be used in situ for metallation. It was found that in carrying out the metallation reaction, a mixed hydrocarbon/ether solvent (toluene/THF) reaction medium gave higher yields of enhanced rac/meso isomer ratio product. The metallation reaction temperature is not critical and can range from about −20° to 120° C. and, preferably, from about 0° to 60° C. Stoichiometric to about a 10% excess amount of metal adduct to ligand salt is preferably used.

The invention is further illustrated by, but is not intended to be limited to, the following examples.

EXAMPLE 1a

ZrCl$_4$ (61.9 grams, 0.266 mol) was slurried in 400 mL of anhydrous toluene N,N,N' N'-Tetramethylethylenediamine (TMEDA) (31.74 grams, 0.273 mol) was added dropwise over 20 minutes. The slurry was stirred overnight and then filtered on a coarse frit. The solids were washed with 50 mL of toluene and dried in vacuo. The yield of ZrCl$_4$(TMEDA) was 88.2 grams (95%).

EXAMPLE 1b

ZrCl$_4$(TMEDA) (35.56 g; 0.102 mol) from Example 1a was placed in a 1 L flask with 260 mL of THF. Most of the solids dissolved. After cooling this material to 0° C., a THF solution of dilithium salt of dimethylsilylbis(2-methylindene)(Et$_2$O) (40.93 grams, 0.102 mol; 300 mL THF) was added dropwise over 3.5 hours. An orange solid precipitated. The reaction was warmed to ambient temperature and stirred overnight. The orange solids were then filtered on a coarse frit, washed with 25 mL of THF, and dried in vacuo. The yield of crude dimethylsilylbis(2-methylindenyl)zirconium dichloride product was 12.24 grams (26%). This solid was extracted with 700 mL of methylene chloride, filtered through a medium frit, and stripped nearly to dryness. Hexanes were added (100 mL) to precipitate the dissolved product. The recrystallized product was filtered on a coarse frit. The purified yield was 8.59 grams (18%). $^1$H NMR in CDCl$_3$ revealed a pure product composed of 93% racemic and 7% meso diasteriomers.

EXAMPLE 2

ZrCl$_4$ (2.26 grams, 0.00970 mol) was slurried in 20 mL of anhydrous toluene. TMEDA (1.23 g, 0.0106 mol) was added dropwise. The slurry was stirred for 17 hours. Dilithium salt of dimethylsilylbis(2-methylindene)(Et$_2$O) (3.87 grams, 0.00961 mol) was dissolved in 27 mL of anhydrous THF and added dropwise to the zirconium slurry over approximately ten minutes. The solution cleared briefly during the addition and then an orange solid precipitated. The reaction was stirred overnight. The orange solids were then filtered on a medium frit, washed with 10 mL of toluene, and dried in vacuo. The yield of crude dimethylsilylbis(2-methylindenyl)zirconium dichloride product was 2.75 grams (60%). After extracting this material into methylene chloride, the purified yield was determined to be 55%. A $^1$H NMR spectrum in CDCl3 showed pure product composed of 93% racemic and 7% meso diasteriomers of dimethylsilylbis(2-methylindenyl)zirconium dichloride product.

EXAMPLE 3

ZrCl$_4$ (2.24 grams, 0.00961 mol) was slurried in 20 mL of anhydrous toluene. TMEDA (1.23 grams, 0.0106 mol) was added dropwise. After less than five minutes, dilithium salt of dimethylsilylbis(2-methylindene)(Et$_2$O) (3.86 grams, 0.00959 mol) in 27 mL of anhydrous THF was added dropwise to the zirconium slurry over approximately fifteen minutes. The solution cleared briefly during the addition and then an orange solid precipitated. The reaction was stirred overnight. The orange solids were then filtered on a medium frit, washed with 10 mL of toluene, and dried in vacuo. The yield of crude dimethylsilylbis(2-methylindenyl)zirconium dichloride product was 2.51 grams (55%). After extracting this material into methylene chloride, the purified yield was determined to be 47.5%. A $^1$H NMR spectrum in CDCl3 showed pure product composed of 93% racemic and 7% meso diasteriomers.

EXAMPLE 4

ZrCl$_4$ (2.95 grams, 0.0127 mol) was slurried in 30 mL of anhydrous toluene. Tetramethyldiaminomethane (TMDAM) (1.42 grams, 0.00139 mol) was added dropwise to the slurry. The slurry was stirred overnight. Dilithium salt of dimethylsilylbis( 2-methylindene)(Et$_2$O) (5.112 grams, 0.0127 mol) dissolved in 35 mL of anhydrous THF was added dropwise to the zirconium slurry at ambient temperature. The solution cleared briefly during the addition and then an orange solid precipitated. The reaction was stirred overnight. The orange solids were isolated on a coarse frit, washed with toluene, and dried in vacuo. The yield of crude dimethylsilylbis(2-methylindenyl)zirconium dichloride product was 3.43 grams (57%). A $^1$H NMR in CDCl3 showed the product to be of similar purity to the crude product of Example 2.

COMPARISON EXAMPLE 1

ZrCl$_4$(THF)$_2$ (2.17 g; 0.00575 mol) was placed in a 100 mL Schlenk flask with 15 mL of anhydrous THF. A portion of the solids dissolved. After cooling this material to 0° C., a THF solution of dilithium salt of dimethylsilylbis(2-methylindene)(Et$_2$O) (2.32 grams, 0.00576 mol; 17 mL THF) was added dropwise over 25 minutes. A dark orange solution resulted. No solids precipitated. The reaction was warmed to ambient temperature and stirred overnight. An aliquot of the clear solution was then stripped to an oily solid and redissolved in THF-d$_8$ for $^1$H NMR. The NMR spectrum showed little or no racemic product.

COMPARISON EXAMPLE 2

ZrCl$_4$(THF)$_2$ (2.17 g; 0.00575 mol) was placed in a 100 mL Schlenk flask with 13 mL of anhydrous toluene. This slurry was stirred with a magnetic stir bar and a solution of dilithium salt of dimethylsilylbis(2-methylindene)(Et$_2$O) (2.32 grams, 0.00576 mol) in 16 mL of THF was added dropwise over 11 minutes. The reaction went clear and the solution became a dark orange. Toward the end of the addition the solution clouded and a precipate began to form. The reaction was stirred overnight. The orange solids were then filtered on a 30 mL medium frit, washed with several mLs of toluene, and dried in vacuo. The yield of orange and brown solids was 1.03 grams (37.5%). After extracting this material into methylene chloride, the purified yield was determined to be 23%. A $^1$H NMR spectrum in CDCl$_3$ showed pure product composed of approximately 93% racemic and 7% meso diasteriomers of dimethylsilylbis(2-methylindenyl)zirconium dichloride.

EXAMPLE 5

ZrCl$_4$ (1.58 grams, 0.0678 moles) was slurried in 16 mL of anhydrous toluene. THF (1.17 grams, 0.0162 moles) was added dropwise. The dropping funnel was then charged with a solution of dilithium salt of dimethylsilylbis(2-methylindene)(Et$_2$O) (2.74 grams, 0.00681 mol) and TMEDA (0.81 grams, 0.00697 mol) in 19 mL of anhydrous THF. After stirring for two hours, the solution of the dilithium salt of dimethylsilylbis(2-methylindene) (TMEDA) was added dropwise to the zirconium slurry. The solution cleared briefly during the addition and then an orange solid precipitated. The reaction was stirred overnight. The orange solids were then filtered on a medium frit, washed with 8 mL of toluene, and dried in vacuo. The yield of crude dimethylsilylbis(2-methylindenyl)zirconium dichloride was 1.26 grams (39%). The crude material provided a typical $^1$H NMR spectrum in CDCl$_3$. The metallocene product was approximately 95% racemic and 5% meso. A purified yield was not determined.

EXAMPLE 6

ZrCl$_4$ (3.04 grams, 0.0130 mol) was slurried in 13 mL of anhydrous toluene. TMEDA (1.57 grams, 0.0135 mol) was added dropwise. THF (8 mL) was then added. The slurry was stirred for 1.5 hours. The dilithium salt of dimethylsilylbisindene(Et$_2$O) (4.85 grams, 0.0130 mol) was dissolved in 28 mL of anhydrous THF and then added dropwise to the zirconium slurry over 25 minutes. The solution cleared briefly during the addition and then an orange solid precipitated. The reaction was stirred overnight. The orange solids were then filtered on a coarse frit, washed with 5 mL of toluene and 5 mL of hexanes, and dried in vacuo. The yield of dimethylsilylbis(indenyl)zirconium dichloride was 4.44 grams (76%). A sample was dissolved in CDCl$_3$ for $^1$H NMR. The NMR spectrum showed pure racemic product.

COMPARISON EXAMPLE 3

ZrCl$_4$ (3.03 grams, 0.0130 mol) was slurried in 13 mL of anhydrous toluene. THF (8 mL) was then added. A dropping funnel was charged with a solution of the dilithium salt of dimethylsilylbisindene (Et$_2$O) (4.85 grams, 0.0130 mol) in 28 mL of anhydrous THF. After stirring for one hour, the ligand solution was added dropwise to the zirconium slurry over 30 minutes. The solution cleared briefly during the addition and then, almost immediately, an orange solid precipitated. The reaction was stirred overnight. The orange solids were then filtered on a coarse frit, washed with 5 mL of toluene and 5 mL of hexanes, and dried in vacuo. The yield of dimethylsilylbis(indenyl)zirconium dichloride was 4.13 grams (71%). A sample was dissolved in CDCl$_3$ for $^1$H NMR. The NMR spectrum showed pure racemic product.

Example 1 demonstrates that by using a diamine adduct in THF, racemic product was produced in contrast to Comparison Example 1 which produced little or no racemic product. Examples 2 to 6 demonstrate the improved yields obtained by using a mixed solvent in combination with the diamine adduct.

What is claimed is:

1. A process for preparing a chiral metallocene, said process comprising reacting a salt of an asymmetric bis(cyclopentadienyl) moiety containing ligand with a chelate diamine adduct of a transition, lanthanide or actinide metal halide in an organic solvent medium so as to produce a chiral metallocene.

2. The process of claim 1 wherein said metal halide is a Group 4–6 metal halide.

3. The process of claim 1, wherein said organic solvent medium is a mixture of an ether and an aromatic hydrocarbon and said chiral metallocene precipitates from said medium.

4. The process of claim 3 wherein said organic solvent medium is a mixture of tetrahydrofuran and toluene.

5. The process of claim 1 wherein said diamine adduct contains a diamine selected from the group consisting of N,N,N' N'-tetramethylethylenediamine and tetramethyldiaminomethane.

6. The process of claim 1 wherein said ligand comprises a pair of cyclopentadienyl moieties, at least one of which is asymmetric, which are joined by a silicon containing bridging group.

7. The process of claim 6 wherein said bridging group contains 1–4 atoms and is selected from the group consisting of silanylene, silaalkylene, oxasilanylene and oxasilaalkylene.

8. The process of claim 7 wherein said bridging group is dimethylsilanylene.

9. The process of claim 7 wherein said chiral metallocene is racemic-dimethylsilyl-bis(2-methylindenyl)zirconium dichloride.

10. The process of claim 7 wherein said chiral metallocene is racemic dimethylsilylbis(indenyl)zirconium dichloride.

11. The process of claim 1 wherein said salt is an alkali metal salt or a magnesium halide salt.

12. A process for preparing a chiral metallocene, said process comprising reacting an alkali metal salt or a magnesium halide salt of an asymmetric bis(cyclopentadienyl) moiety containing ligand with a chelate diamine adduct of a Group 4 metal halide in a mixed ether-aromatic hydrocarbon solvent medium so as to produce a chiral metallocene.

13. The process of claim 12 wherein the chelate diamine adduct is an adduct of TMEDA or TMDAM and zirconium tetrachloride.

14. The process of claim 13 wherein said salt is the dilithium salt of dimethylsilylbis(2-methylindene) and said chiral metallocene is racemic-dimethylsilylbis(2-methylindenyl)zirconium dichloride.

* * * * *